(12) United States Patent
Shiff et al.

(10) Patent No.: US 6,201,028 B1
(45) Date of Patent: Mar. 13, 2001

(54) METHODS AND COMPOSITIONS FOR PREVENTION AND TREATMENT OF ATHEROSCLEROSIS AND HYPERLIPIDEMIA WITH NON-STEROIDAL ANTI-INFLAMMATORY DRUGS

(75) Inventors: Steven Shiff, New York; Edward A. Fisher, Scarsdale; I. Bernard Weinstein, Englewood; Hayes M. Dansky, Larchmont; Urnani Reiss, New York, all of NY (US)

(73) Assignees: The Rockefeller University; Mt. Sinai School of Medicine; Columbia University, all of New York, NY (US)

( * ) Notice: Subject to any disclaimer, the term of this patent is extended or adjusted under 35 U.S.C. 154(b) by 0 days.

(21) Appl. No.: 09/208,613

(22) Filed: Dec. 8, 1998

(51) Int. Cl.[7] .................................................. A01N 43/40
(52) U.S. Cl. .......................................... 514/824; 514/569
(58) Field of Search ................................. 514/165, 338, 514/420, 458, 460, 567, 568, 569, 824

(56) References Cited

U.S. PATENT DOCUMENTS 5,811,438 * 9/1998 Hellberg et al. ..................... 514/458

OTHER PUBLICATIONS

CA 132:98131, Zheng, May 1998.*
CA 129:81020, Parthasarathy, 1998.*
Conn's Current Therapy, W.B. Saunders Company, Philadelphia, pp. 504–509, 1992.*
CA 129:255000, Falk et al., Oct. 1998.*
CA 114:49589, Dennick, Jun. 1990.*
CA 87:127635, Dincol et al., 1976.*
CA 94:25044, Vitic et al., 1979.*
CA 117:149923, Williams et al., 1992.*
Abstract Zheng, Liquo, May 1998.
Abstract Parthasarathy, Sampath 1998, 1(1) pp. 45–51.
Rakes, Robert, Conn's Current Therapy Philadelphia W.B. Saundes Co. 1992, pp. 504–509.
Abstract Falk et al., Oct. 1998.
Abstract Dennick L.G., Jun. 1990.
Abstract Dincol et al. 1976, 9(1) 11–15.
Abstract Vitic et al. 1979 15(3) pp. 504–506.
Abstract Willliams et al. 1992, 94(23), pp. 153–159.
Abs Xue et al, 1998, 27(1) pp. 36–37, CA 129:270288.
Abs Rogalla et al, Feb. 1994 CA 120:183024.
Abs 1997, 337 (6), pp. 365–372 CA 127:185634.
Abs Konneh et al 1995, 113(1) 29–39 CA 122:212746.
Abs Demopolous July 1993 CA 119:131529.
Abs Lee et al 1996, 37(3) 32–332 CA 125:292744.
Abs Herbert et al 1998 83 (3) 512–518 CA 129:225307.
Cell 1992, 71: 343–353.
Circulation 1993, 88:A9.
Arteriosclerosis Thromb. 1994, 14:1873.
Nature 1992, 358:15.
Biochem. Pharmacol 1996, 52:237–245.
Adv. Drug Res 1977, 12: 90–245.
Cell 1995, 80:285.
Science 1996, 272:685–688.

* cited by examiner

Primary Examiner—Edward J. Webman
(74) Attorney, Agent, or Firm—Rashida A. Karmaly Esq

(57) ABSTRACT

Methods and compositions for the prevention and/or treatment of cardiovascular diseases, the methods comprising administering to individuals in need thereof, an effective amount of a non-steroidal anti-inflammatory drug alone or in combination with other conventional therapies to induce apoptosis, reduce proliferation, induce quiescence, inhibit cell migration, or influence cell differentiation of the cells in the vascular wall and or/induce hypolipidemia.

4 Claims, 6 Drawing Sheets

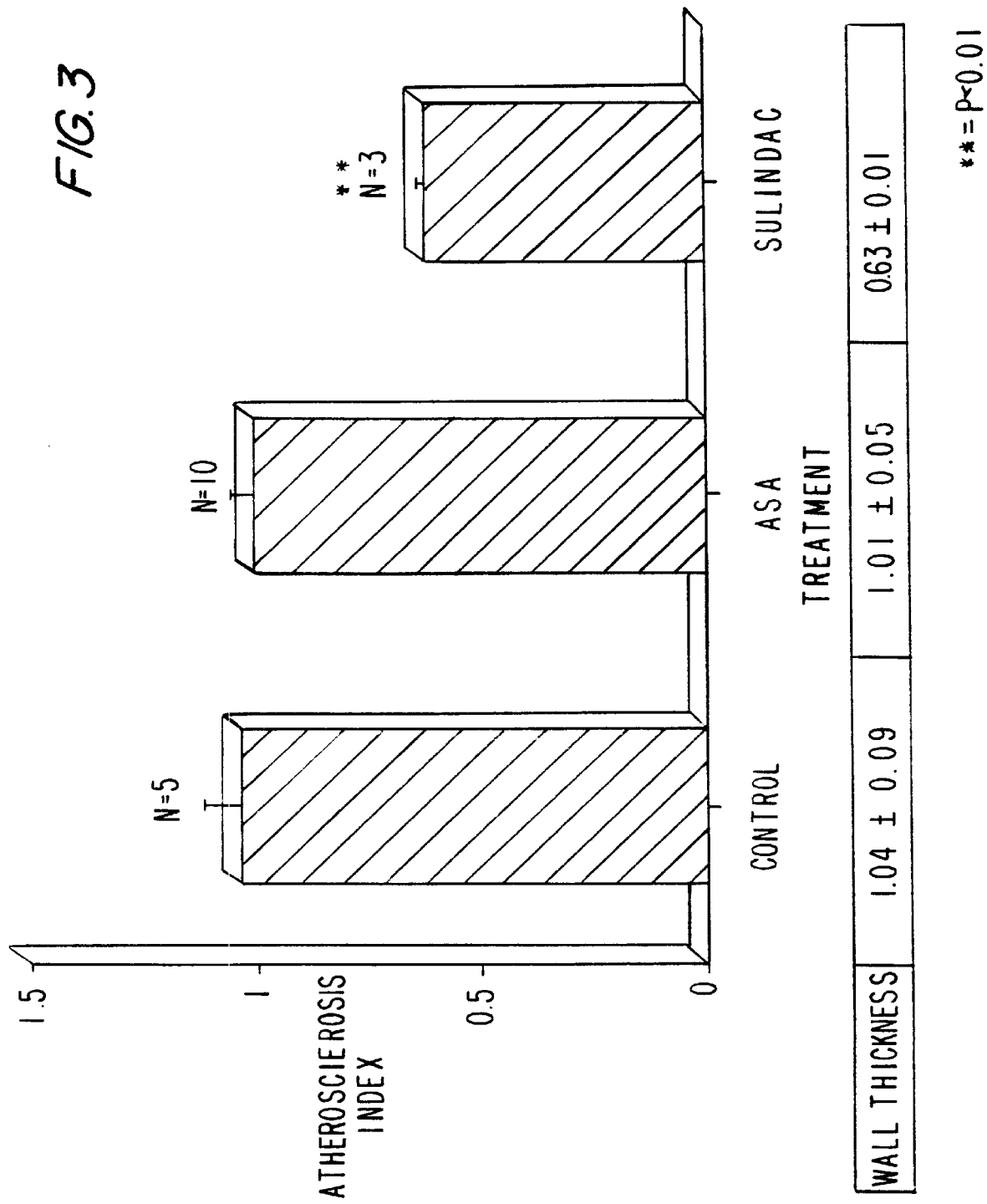

FIG.4C ASPIRIN
FIG.4B SULINDAC
FIG.4A CONTROL

APOE KO + SULIDAC
FEMORAL ARTERY WIRE INJURY (4 WK)

METHODS AND COMPOSITIONS FOR PREVENTION AND TREATMENT OF ATHEROSCLEROSIS AND HYPERLIPIDEMIA WITH NON-STEROIDAL ANTI-INFLAMMATORY DRUGS

1. INTRODUCTION

The invention relates generally to methods and compositions for the prevention and treatment of arterial lesions with the administration of non-steroidal anti-inflammatory drugs (NSAIDs). The present invention relates to methods and compositions for preventing and treating atherosclerosis or restenosis in mammals, by inducing or stimulating apoptosis, reducing proliferation, inducing quiescence, inhibiting cell migration, or influencing cell differentiation of the cells of the vessel wall that contribute to arterial lesions. In particular, the methods and compositions of the invention are useful in the stimulation of cell death and/or the inhibition of cell proliferation or migration of vascular cells or other target cells that contribute to arterial lesion formation. In the practice of the invention, NSAIDs can be further applied to induce removal of lipoprotein particles from the plasma, to act as lipid-lowering agents, to enhance the function of lipid-lowering agents, and/or to act as antioxidants or stimulate or enhance the function of antioxidants.

2. BACKGROUND OF THE INVENTION

The complications of arteriosclerosis in the United States account for about one half of all deaths. Three fourths of arteriosclerosis-related deaths are the result of coronary artery disease (CAD), also termed ischemic heart disease. Arteriosclerosis-related diseases are also the leading cause of permanent disability and account for more hospitalization than any other illness. Atherosclerosis or the development of atheromatous plaques in large and medium-sized arteries, is the most common form of arteriosclerosis. Preventing formation or growth of atherosclerotic plaques is widely regarded as a promising approach to the primary and secondary prevention of CAD.

The primary initiating factors in the formation of atheromatous plaques are the recruitment of monocytes into the vascular wall and the proliferation and migration of smooth muscle cells from the media to the intima of the arterial wall. Presumably, these events are accelerated by the deposition of cholesterol and other lipids carried in by the plasma lipoproteins, particularly LDL. The atherogenic process, at first, produces simple atheromatous plaques, as the monocytes differentiate into macrophages and they and the smooth muscle cells take up lipids. Later, lipids, collagen, elastic fibers and proteoglycans are deposited in the extracellular space. Hemorrhage, necrosis, and calcification occur at still later stages. It has been suggested that the vessel wall thickness is a conserved parameter, homeostatically regulated by the balance between cell renewal and cell death. Thus, as vascular smooth muscle proliferation increases in response to specific physiologic signals, apoptosis (or programmed cell death) increases in compensation to conserve total cell mass.

If pathophysiological signals for proliferation continue to be exerted, for example, when hyperlipidemia is chronically maintained, mechanisms to limit the expansion of cell mass in the arterial wall may become overwhelmed. The end result is that the vessel wall thickness expands and the lumen of the artery narrows, resulting in the secondary complications of reduced blood flow to the tissues and organs downstream of the stenotic vessel. A reduction in cell proliferation or the induction of apoptosis in this early stage of development of the atherosclerotic lesion may therefore be beneficial in limiting the increased population of macrophages and smooth muscle cells or other cells. However, in the later stage of an atherosclerotic lesion, factors promoting cell death may destabilize the plaque and cause the release of pro-thrombotic material into the extracellular space. This in turn, may enhance the tendency toward platelet aggregation and formation of detrimental clots.

Therefore, cell death may have anti- or pro-atherogenic effects depending on the type and evolution of the atherogenic lesion.

Similarly, the expanded population of vascular cells after interventions intended to increase coronary perfusion, such as but not limited to angioplasty, may represent an imbalance of cell proliferation over cell death, resulting in restenosis of the vessel.

The stimulated platelet synthesizes thromboxane (TX) $A_2$, which can aggregate other platelets and constrict vascular smooth muscle. These platelets also release ADP and serotonin, which likewise serve to recruit other platelets. Thrombin generated in the vicinity of a platelet plug or thrombus, as well as platelet endoperoxides, can act as stimuli for prostacyclin ($PGI_2$) production in the vasculature. Since $PGI_2$ has anti-aggregating effects on platelets, there emerged a therapeutic strategy to balance $PGI_2$ and $TXA_2$ production in an attempt to regulate aggregability of platelets in vivo. An ideal therapeutic situation is one in which $TXA_2$ production is abolished but $PGI_2$ synthesis continues unabated or is stimulated. This led to development of specific thromboxane synthetase inhibitors or prostacyclin synthetase stimulators. For example, aspirin, a non-steroidal anti-inflammatory agent NSAID) and an anti-thrombotic agent irreversibly acetylates platelet cyclooxygenase and reverses the platelet aggregation, although cyclooxygenase in vascular tissues has been found to be 20-to 40- fold less sensitive to aspirin inactivation than the cyclooxygenase in platelets. Since a balance between $PGI_2$ and $TXA_2$ production is important, its manipulation by pharmacologic agents, including, but not limited to, other NSAIDs (e.g., ibuprofen sulindac, sulindac sulfide, sulindac sulfone, flurbiprofen, indomethacin, aspirin, naproxen, meclafenamic acid, or piroxicam) has been used extensively in retarding a thrombotic diathesis. However, heretofore, the use of NSAIDs in the control of cell death, cell differentiation, migration, or proliferation in an animal model of human atherosclerosis or restenosis has not been identified, much less considered as therapeutic interventions for the prevention and treatment of arterial lesions in various forms of coronary artery disease. Heretofore, the use of NSAIDs in atherosclerosis other than to interfere with thrombotic or platelet aggregatory mechanisms has not been identified, much less considered.

3. SUMMARY OF THE INVENTION

In accordance with the invention, methods and compositions are provided for the prevention and treatment of arterial lesions or preventing restenosis by administering non-steroidal anti-inflammatory drugs. The compositions include NSAIDs alone or in combination with lipid lowering agents or diets or antioxidants or angioplastic procedures. The preventive and/or treatment methods can involve inducing apoptosis, reducing proliferation, inducing quiescence, inhibiting macrophage migration, or influencing cell differentiation, and/or clearance of lipoproteins to thereby prevent and/or treat arterial lesions and provide a variety of health benefits.

The present invention can provide a method of preventing arterial lesions and atherosclerosis or restenosis by applying NSAIDs which induce apoptosis, reduce proliferation, induce quiescence, inhibit macrophage and smooth muscle cell migration, or influence cell differentiation in the vessel wall. The method can include subjecting the vascular cells to an effective amount of NSAIDs to trigger and induce programmed cell death, reduce proliferation, induce quiescence, inhibit macrophage and smooth muscle cell migration, or influence cell differentiation and prevent occlusive or thrombotic events in arteries.

The present invention can also provide a therapeutic method for the treatment of arterial lesions and atherosclerosis or restenosis, associated with apoptosis, proliferation, monocyte/macrophage and smooth muscle cell migration, or differentiation of vascular cells by administering an effective amount of an NSAID to induce apoptosis, reduce proliferation, induce quiescence, inhibit macrophage and smooth muscle cell migration, or influence cell differentiation of cells that contribute to atherosclerosis. In accordance with the invention, an effective amount of one or more NSAID is administered to induce the removal of lipoproteins from the plasma to thereby prevent and/or treat a variety of atherosclerotic conditions.

According to an additional aspect of the present invention, there is provided a method to induce apoptosis, reduce proliferation, induce quiescence, inhibit macrophage and smooth muscle cell migration, or influence cell differentiation of cells that contribute to a complex or unstable plaque in atherosclerosis by administering NSAIDs along with an antithrombotic therapy, including the administration of an effective amount of an antithrombotic agent such as heparin or warfarin.

According to yet another aspect of the present invention, there is provided a method to induce apoptosis, reduce proliferation, induce quiescence, inhibit macrophage and smooth muscle cell migration, or influence cell differentiation of cells that contribute to atherosclerosis by administering NSAIDs along with antioxidant therapy, including the administration of an effective amount of an antioxidant such as vitamin A, vitamin E, N-acetylcysteine, glutathione, vitamin C, and/or magnesium gluconate.

According to yet another aspect of the present invention, there is provided a method to induce apoptosis of cells that contribute to atherosclerosis including the application of NSAIDs in combination with a conventional therapeutic regimen including by-pass surgery, angioplasty, beta-blocker therapy, calcium channel antagonists, magnesium, thrombolytic therapy, antithrombotic therapy or drug therapy to treat hyperlipidemia.

In accordance with the invention, compositions for the induction of apoptosis reduce proliferation, induce quiescence, inhibit macrophage and smooth muscle cell migration, or influence cell differentiation in cells that contribute to atherosclerosis and for induction of clearance of lipoproteins in plasma are also provided and include, NSAIDs used alone or in combination with conventional therapeutic regimens used to prevent and/or treat arterial lesions or restenosis.

The present invention is based on the unexpected discovery that NSAIDs are effective in inducing apoptosis, reducing proliferation, inhibiting migration, or influencing differentiation of cells that contribute to atherosclerosis and in inducing clearance of plasma lipoproteins or otherwise promoting hypolipidemia.

It is the object of the present invention to provide compositions and/or a method for inducing apoptosis, reducing proliferation, inhibiting migration, or influencing differentiation of cells that contribute to atherosclerosis.

It is the object of the present invention to provide compositions and/or a methods for inducing cell quiescence, reducing proliferation, inhibiting migration, or influencing differentiation in the cells of the vessel wall that contribute to arterial lesions and restenosis.

It is the object of the present invention to provide compositions and/or therapeutic methods for preventing recurrence of atherosclerosis after procedures designed to increase coronary artery blood flow, such as by-pass surgery, reperfusion or angioplasty.

It is also an object of the present invention to provide compositions and/or methods for inducing apoptosis and cell quiescence in cells of the vessel wall using NSAIDs alone or in combination with an effective amount of one or more conventional therapies or anti oxidants.

It is the object of the present invention to provide compositions and/or methods for inducing plasma lipoprotein clearance or otherwise promoting hypolipidemia.

Still other objects and advantages of the invention will in part be obvious and will in part be apparent from the specification and working examples described herein.

4. BRIEF DESCRIPTION OF DRAWINGS

For a fuller understanding of the invention, reference is made to the following description taken in connection with the accompanying drawings, in which:

FIG. 3 is a diagram illustrating the Atherosclerosis Index (measured as wall thickness) in mice Apo E (-1-) at 18 weeks after feeding a western diet to control mice, or a western diet with aspirin or a western diet with sulindac.

FIG. 4(a) is a cross sectional view of the aortic root (enlarged ×40) in control mice, showing narrowing of the lumen. The stained plaque is a thickening of the arterial vessel wall.

FIG. 4(b) is a similar cross sectional view of the aortic root (enlarged ×40) in mice treated with sulindac, showing much less narrowing of the lumen in comparison with that in FIG. 4(a).

FIG. 4(c) is a similar cross sectional view of the aortic root (enlarged ×40) in mice treated with aspirin, showing narrowing of the lumen that lies intermediary between that in FIG. 4(a) and FIG. 4(b).

5. DETAILED DESCRIPTION OF THE INVENTION

Figure 1:
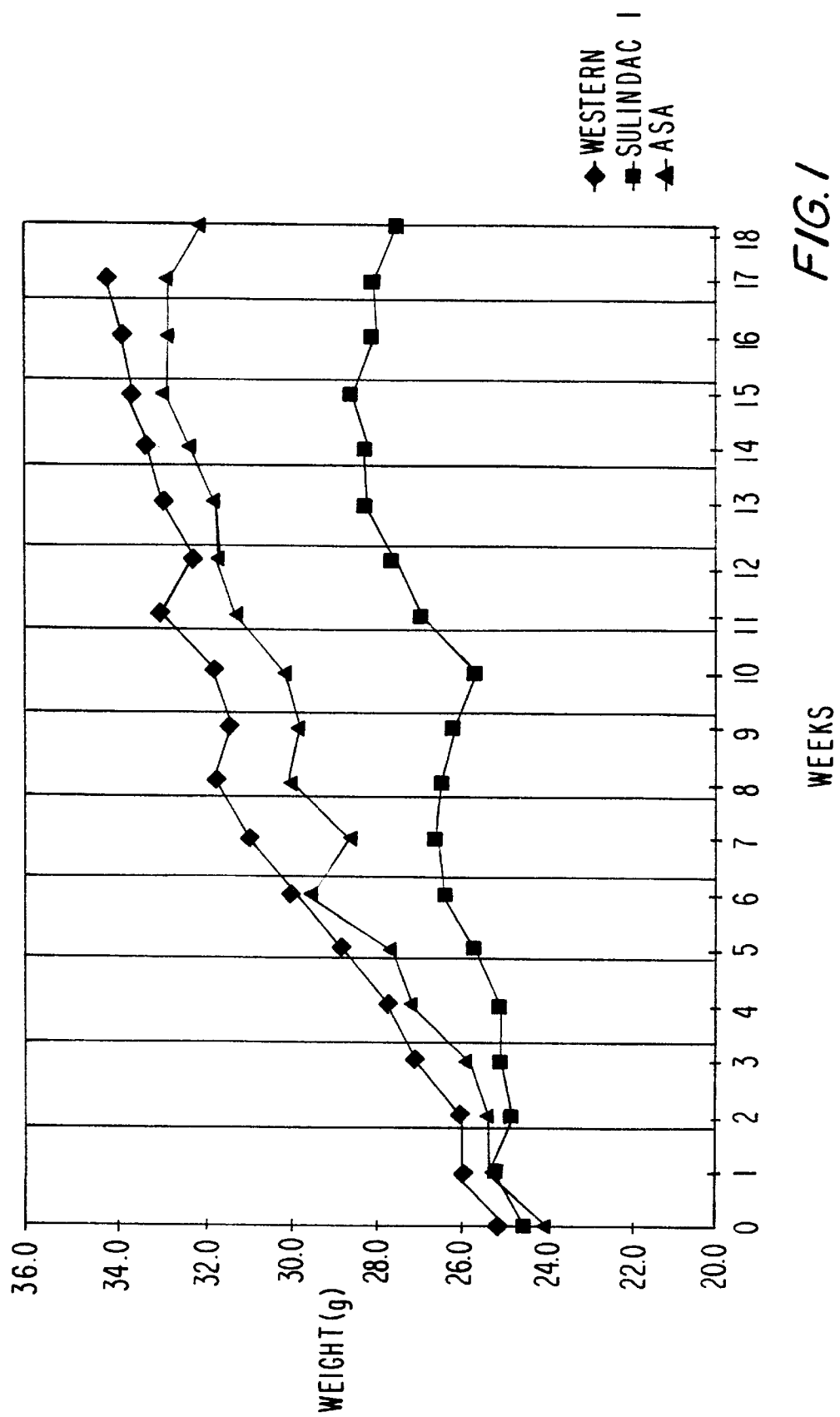
FIG. 1 is a diagram illustrating the average body weight Apo E (-1-) of mice fed a western diet alone, a western diet with aspirin or a western diet with sulindac over a period of 18 weeks.

The present invention generally pertains to compositions and novel methods for preventing and treating arterial lesions and atherosclerosis and restenosis using one or more NSAIDs in an effective amount for inducing apoptosis, reducing proliferation, inhibiting migration, or influencing cell differentiation in treated cells and hypolipidemia in plasma. The atherosclerosis prevention and therapeutic methods of the invention are fundamentally based upon a newly-discovered effect of NSAIDs on apoptosis, proliferation, migration, or differentiation of cells that contribute to atherosclerosis and on newly discovered hypolipidemic effect of NSAIDs in plasma. The present invention also provides compositions and methods for inducing cell quiescence in the cells of the vessel wall that contribute to the arterial lesions.

5.1. Risk Factors

Clinical and epidemiologic evidence indicates that many factors are associated with coronary heart disease and the acceleration of atherosclerosis, regardless of the underlying primary pathologic change. The most important risk factors for atherosclerosis are advanced age, elevated plasma cholesterol and low-density lipoprotein cholesterol, high arterial blood pressure, diabetes and cigarette smoking.

The Apo-E deficient mouse is the first mouse model of atherosclerosis with pathology similar to that of human atherosclerosis (Cell 1992, 71:343–353). Serum cholesterol levels in the mice maintained on a chow diet are five times higher than those of control littermates. Apo-E, which is made primarily in the liver, is a surface constituent of lipoprotein particles and a ligand for lipoprotein recognition and clearance by lipoprotein receptors (Science 1996, 272:685–688). ApoE-deficient mice have delayed clearance of lipoproteins, and on a low-cholesterol, low-fat diet, their cholesterol levels reach 400 to 600 mg/dl as a result of accumulation of chylomicron and very low-density lipoprotein (VLDL) remnants enriched in esterified and free cholesterol (Circulation 1993, 88:A9). These mice develop not only fatty streaks but also widespread fibrous plaque lesions at vascular sites typically affected in human atherosclerosis (Arterioscler. Thromb. 1994, 14;1873). Lesions form at the base of the aorta and the lesser curvature of the thoracic aorta, at the branch points of the carotid, intercostal, mesenteric, renal and iliac arteries, and in the proximal coronary, carotid, femoral, subclavian, and brachiocephalic arteries. Lesions begin at 5 to 6 weeks of age with monocyte attachment to the endothelium in lesion-prone areas and transendothelial migration. Fatty streak lesions begin to appear at 10 weeks, and intermediate lesions containing foam cells and spindle-shaped smooth muscle cells appear at 15 weeks. Fibrous plaques appear after 20 weeks and consist of a necrotic core covered by a fibrous cap of smooth muscle cells surrounded by elastic fibers and collagen. In older mice, fibrous plaques progress. In some advanced lesions there is partial destruction of underlying medial cells with occasional aneurysm formation, and in others calcification occurs in the fibrous tissue. Extensive fibro-proliferation can narrow the lumen, even to the point of occlusion of vessels.

Atherosclerosis can be exacerbated by a high-cholesterol or high-fat diet. This effect is mimicked in the ApoE-deficient mice when these mice are fed a western-type diet as described below in Section 6.

5.1.3. Cell Proliferation

The structural organization of a vessel wall consists of three layers: the intima, the media, and the adventitia. The intima is a single continuous layer of endothelial cells and associated basement membrane. The media is a layer of smooth muscle cells separated from the intima by a sheet of elastic fibers, the internal elastic lamina. The external elastic lamina forms the border between the media and the adventitia. The response to injury hypothesis of atherosclerosis postulates that injury to the endothelium is the primary event in the formation of an atherosclerotic lesion. Smooth muscle cells then migrate from the media into the intima through fenestrae in the internal elastic lamina and undergo active proliferation within the intima. High levels of cholesterol and oxidized lipoproteins trigger and stimulate the proliferation of smooth muscle cells. Adherence of platelets to exposed connective tissue may cause the formation of platelet aggregates or microthrombi. If the lesion progresses further, fibrosis, lipid deposition, necrosis and calcification may ensue to yield a complicated plaque. The atherogenic process involves the proliferation, in the arterial wall, of some major cell types found in the plaque: vascular smooth muscle cells and macrophages. In both primary and re-stenoic or recurrent atherosclerotic lesions however, vascular smooth muscle cells tend to be the earliest and most robust responders to atherogenic stimuli, such as hyperlipidemia and endothelial cell damage. Thus, as proliferation of vascular smooth muscle cells increases in response to specific physiologic signals, there is a need to balance cell renewal and cell death in order to conserve the total cell mass in the vessel wall. If stimuli for proliferation continue to be exerted, for example, through chronic hyperlipidemia, then eventually cell death or apoptosis can no longer offset the inducement to cell proliferation resulting in the vessel wall thickness becoming dysregulated. The end result is that the vessel wall thickness expands and the lumen of the artery narrows, resulting in the secondary complications of atherosclerosis, for example, reduced blood flow to the organs downstream of the stenotic vessel.

5.1.4. Apoptosis

Apoptosis, a genetically regulated form of cell death, is a general property of most if not all cells. It is necessary in tissues of multicellular organisms to achieve an adequate balance between the sufficient survival of cells and the overwhelming proliferation and expansion of the cell mass, ie, cell mass homeostasis.

From the perspective of arterial lesions and atherosclerosis, apoptosis or programmed cell death may be both a mechanism which suppresses plaque formation and as a predominant pathway in anti-atherosclerotic therapy. Two major endogenous regulators of apoptosis have been identified, for example, the wild-type p53 protein which functions as an inducer of cell death especially in response to DNA damaging events and reciprocally, Bcl-2 which has an important antiapoptotic function (Nature 1992, 358:15; and Cell 1995, 80:285).

It is important to note that induction of apoptosis in the atherosclerotic lesion may not always be beneficial; for example, in a complex plaque, apoptosis of lipid-laden macrophages and monocytes may result in release of oxidized pro-thrombotic lipid or lipid-associated materials into the extracellular space which in turn may result in formation of occlusive thrombi. Thus, the effects of apoptosis may be anti- or pro-atherogenic depending on the evolution of or the stage of development of the arterial lesion. For example, since the early events of plaque formation depend on proliferation of vascular smooth muscle cells, increasing apoptosis of those cells with NSAIDs, before the arterial wall thickness exceeds a threshold level reduces the extent of lesions and thus improves the vessel patency. On the other hand, if a lesion were reasonably well-established, increasing apoptosis may destabilize the plaque, and result in myocardial inschemia or infarction.

In a severely stenotic vessel that has been subjected to angioplasty, increasing apoptosis with NSAIDs prolongs the time the treated vessel remains patent since an early event in re-stenosis is proliferation of vascular smooth muscle cells.

Cellular antioxidant defense mechanisms such as the reactive-oxygen scavenger enzymes superoxide dismutase, glutathione peroxidase and catalase can control apoptosis. For example, there is evidence that Bcl-2 inhibits apoptosis through the regulation of glutathione peroxidase. Thus, the present invention also includes a method for inducing apoptosis in vascular smooth muscle cells using a combination of NSAIDs and antioxidant therapy. Suitable antioxidants include, but are not limited to, one or more of N-acetylcysteine, vitamin E, glutathione, vitamin C and/or magnesium gluconate. Patient dosages for administration would vary according to the antioxidant used, for example, the adult dose for vitamin E would range from 200 I.U. to 1000 I.U. per day.

5.2 Non-Steroidal Anti-Inflammatory Drugs

Non-steroidal anti-inflammatory drugs have anti-inflammatory, analgesic and antipyretic activities. They are used clinically for the treatment of patients with acute arthritis, chronic arthritis such as rheumatoid arthritis, osteoarthritis, gouty arthritis, ankylosing spondylitis, tendonitis, bursitis and inflammatory arthritis. In addition to their therapeutic use in these conditions, NSAIDs have been found to reduce the risk of development and mortality of oesophageal, gastric, and colorectal cancer.

5.2.1. Cyclooxygenase Inhibitors

Members of the structurally diverse class of drugs known as NSAIDs are thought to exert their anti-inflammatory, antipyretic and antianalgesic effects by inhibition of cyclooxygenases, the rate-limiting enzymes that catalyze the formation of prostaglandin precursors from arachidonic acid. Prostaglandins play a role in the control of cell proliferation and regulation of immune functions. However, doses of NSAIDs required to suppress inflammation may exceed substantially the doses necessary to inhibit prostaglandin synthesis, suggesting that the anti-inflammatory properties of these drugs may be achieved through additional identified mechanisms. For example, NSAIDs including, but not limited to aspirin, indomethacin, naproxen, sulindac and piroxicam reduced proliferation and altered morphology of HT-29 human colon adenocarcinoma cells. A common property of NSAIDs to decrease tumor cell proliferation, alter morphology, cause cells to accumulate in the $G_0/G_1$ phase of the cell cycle and increase the rate of apoptosis tends to suggest common targets of the drugs of the NSAIDs tested (aspirin, indomethacin, sulindac and its metabolites, naproxen and piroxicam). In addition, certain NSAIDs may act independent of their ability or inability to inhibit cyclooxygenase. In the HCT-15 cultured colon cancer cell line the NSAIDs, sulindac and piroxicam exerted their antiproliferative effect independent of prostaglandin synthesis (Biochem. Pharmacol. 1996, 52:237–245).

Heretofore, the only NSAID recommended for use in the treatment of coronary artery disease is aspirin. Aspirin has become a critical component of acute myocardial therapy. Aspirin irreversibly acetylates the platelet cycolooxygenase enzyme and elicits its effect for the life of the platelet. Aspirin has also been used for secondary prevention of recurrent cardiovascular events following acute myocardial infarction. In the case of platelets, even a small dose of aspirin inhibits prostaglandin and thromboxane production.

In the present invention, administration of NSAIDs resulted in inhibition of development of atherosclerotic lesions, and in reducing the plasma levels of cholesterol, and in preventing restenosis. More specifically, administration of sulindac to ApoE-deficient mice maintained on a western diet significantly inhibited the development of atherosclerotic lesion and restenosis. Unexpectedly, administration of sulindac also reduced the level of cholesterol in the plasma. See infra, Section 6. In addition, sulindac also inhibited restenosis. See infra, Section 7.

Sulindac (Clinoril®) is a prodrug that is metabolized after p.o. administration to either a sulfide or sulfone derivative. The sulfide is known to be a potent inhibitory agent of cyclooxygenase and is exclusively responsible for the anti-inflammatory properties of sulindac. The sulfone does not inhibit cyclooxygenase and does not have anti-inflammatory properties. (Adv. Drug Res. 1977, 12:90–245).

Similarly administration of aspirin to ApoE-deficient mice maintained on a western diet inhibited the atherosclerotic index but to a lesser extent than observed in the group treated with sulindac. Aspirin also unexpectedly reduced the level of cholesterol in the plasma. See infra, Section 6. Thus, aspirin and sulindac and NSAIDs in general are useful for the prevention and treatment of hyperlipidemia and atherosclerotic lesions and restenosis.

5.2.2. Choice of NSAIDs

The present invention provides a number of different structurally diverse class of drugs known as NSAIDs which have the ability to induce apoptosis, reduce proliferation, inhibit migration, or influence cell differentiation in cells of the vascular wall and which increase the clearance of cholesterol and thereby to lower plasma cholesterol levels, for example, sulindac, sulindac sulfide, sulindac sulfone, aspirin, indomethacin, ibuprofen, meclafenamic acid, flurbiprofen, naproxen or piroxicam.

5.3 Pharmaceutical Preparations and Methods of Administration

The NSAIDs that induce apoptosis, reduce proliferation, inhibit migration, or influence cell differentiation of cells in vessel walls and/or induce hypolipidemia, can be administered to a patient at therapeutically effective doses to prevent or treat atherosclerotic lesions or restenosis. A therapeutically effective dose refers to that amount of the compound sufficient to result in prevention or treatment of symptoms or complications of atherosclerosis.

5.3.1. Dosage and Formulation

Pharmaceutical compositions of NSAIDs may include the currently available formulations or may be formulated in different proportions in combination, using one or more physiologically acceptable carriers or excipients.

Thus, the NSAIDs alone or in combination with other NSAIDs, antioxidants or other conventional therapies e.g., the cholesterol lowering drugs, may be formulated with pharmaceutically compatible counterions, a form in which they are merely water-soluble.

The pharmaceutical compounds may be administered intravenously, intraarterially, intraperitioneally, subcutaneously, sublingually, intramuscularly, intrathecally, orally, rectally, topically or by aerosol.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparation for oral administration may be suitably formulated to give controlled release of the active compound.

For buccal admistration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Patient dosages for oral administration of NSAIDs will vary for each compound, for example, for sulindac, may range from 1–1000 mg/day, commonly 100–300 mg/day, and typically from 200–300 mg/day. Stated in terms of patient body weight, usual dosages of sulindac range from 0.02 to 12.5 mg/kg/day, commonly from 1.25–3.75 mg/kg/day typically from 2.5 to 3.75 mg/kg/day. Stated in terms of patient body surface areas, usual dosages range from 0.5–600 mg/m$^2$/day, commonly from 66–200 mg/m$^2$/day.

It may be necessary to adjust the dosage amount and to provide plasma levels of the active moiety which are sufficient to maintain the beneficial effects on the cells of the vessel wall and the hypolipidemic effect in the plasma.

6. EXAMPLE

Effects of Sulindac and Aspirin on Development of Arterial Lesions in the Apo-E Deficient Mice The Apolipoprotein E knock-out mouse model is a valuable animal model to test the effect of NSAIDs on apoptosis, proliferation, quiescence, migration and differentiation of cells that contribute to atherosclerosis. ApoE is an apoprotein on the surface of atherogenic lipoproteins that serves as a ligand for certain receptors in key tissues. ApoE-induced signaling via these receptors, particularly by the hepatic LDL receptor, induces the removal of ApoE-containing lipoprotein particles from the plasma. When both copies of ApoE are knocked-out by gene targeting, the atherogenic proteins, e.g., VLDL and chylomicron remnants accumulate in the plasma and are deposited at accelerated rates in vascular tissue. The result is the relatively rapid formation of complex atherosclerotic lesions in the aorta, which have the essential characteristics of human plaques, namely proliferation and migration of vascular smooth muscle cells and macrophage foam cell formation. This model is highly suitable for pre-clinical screening of drugs, metabolic factors and other modalities aimed at preventing and/or treating atherogenesis and restenosis.

6.1. Materials and Method

Thirty six week old ApoE-knockout mice were used and given the following dietary regimen and treatment: Group 1-western type diet (containing 42% by calories % fat and 0.15% (w/w) cholesterol); Group 2-western type diet plus Sulindac at a concentration of 400 mg/kg diet and Group 3-western type diet plus aspirin at a concentration of 400 mg/kg diet. The body weight was monitored on a weekly basis. Plasma cholesterol was measured at 8 and 17 weeks after the start of the experiment by routine methods. At the termination of the experiment, the heart-aortic combined structure was sectioned from each animal and stained for lipid content and for quantifying the cross-sectional area of the lesions by computer-aided planimetry (Plump et al., Cell 1992, 71:343–353). The sections were stained with hematoxylin and eosin for routine morphological assessment (e.g., foam cell vs. Advanced complex plaque).

6.2 Results

Mean body weight of mice in the groups receiving NSAID treatments was lower than in the control mice. Body weight in mice receiving Sulindac was lower than the Aspirin group. Sulindac and aspirin both lowered the plasma cholesterol levels compared with the control group at eight weeks and 17 weeks after the start of the diets and treatments indicating that these NSAIDs have a hypolipidemic effect in those ApoE knock-out mice. FIG. 1 and Table 1. The effect of sulindac compared to control on total cholesterol at 17 weeks was found to be statistically significant (p=0.0015).

TABLE 1

|  | Total Cholesterol 8 wks | n | Total Cholesterol 17 wks | n |
|---|---|---|---|---|
| Control | 1777.09 ± 134.06 | 8 | 1334.71 ± 132.74 | 7 |
| ASA | 1430.42 ± 184.03 | 12 | 822.93 ± 84.34 | 11 |
| Sulindac | 1088.59 ± 177.01 | 10 | 433.52 ± 162.20 | 5 |

Figure 2:
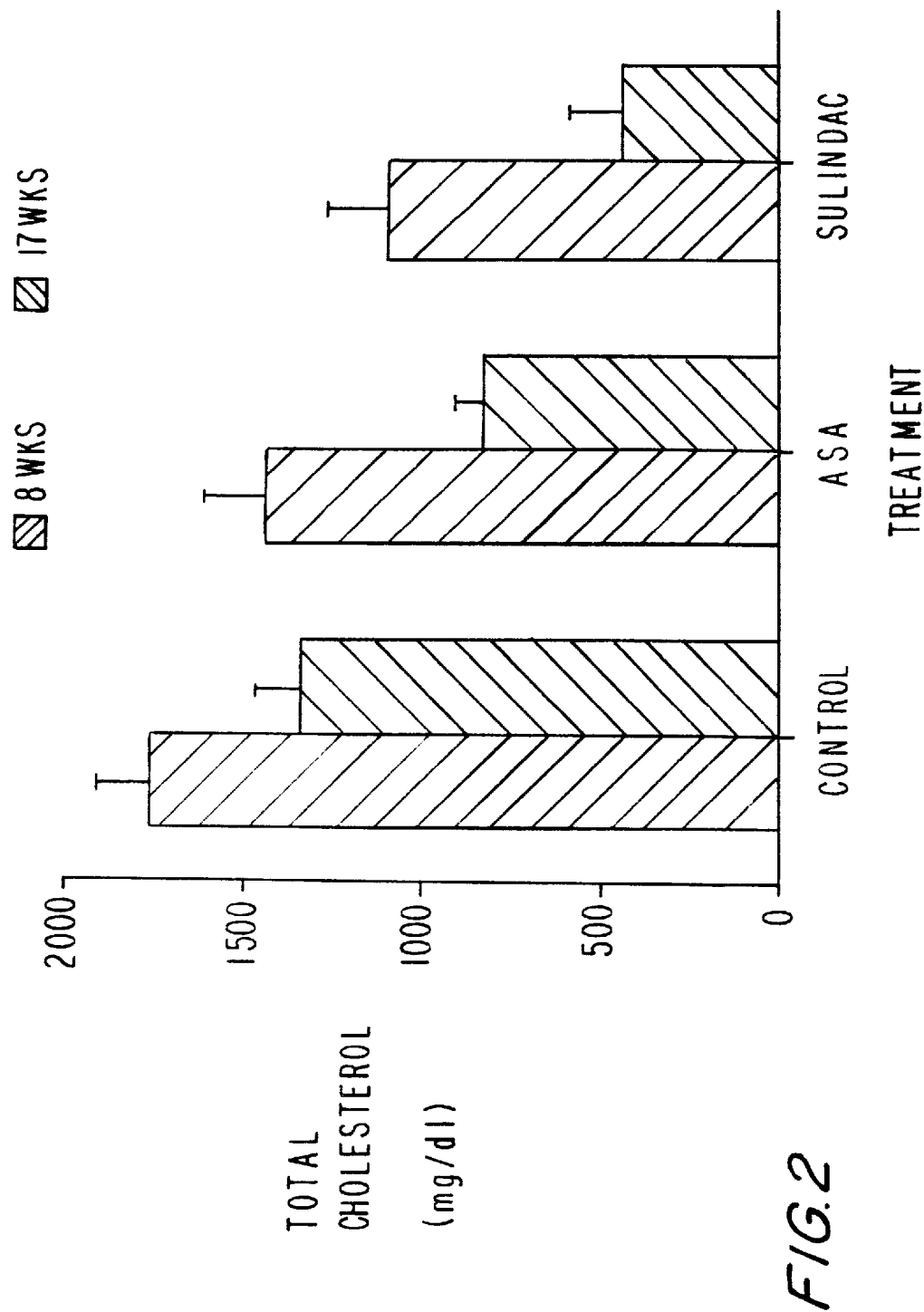
FIG. 2 is a diagram illustrating the total plasma cholesterol (mg/dl) in mice Apoe (-1-) at 8 weeks and 17 weeks after feeding them a western diet only (control), a western diet with aspirin or a western diet with sulindac.
Figure 5A:
FIG. 5 is a series of cross-sectional views of the femoral artery in control mice maintained on the Western diet in: (A) noninjured mice, (B) 1 hour after mechanical injury, (C) 24 hours after mechanical injury, (D) 1 week after mechanical injury, (E) 2 weeks after mechanical injury and (F) 4 weeks after mechanical injury.
Figure 5B:
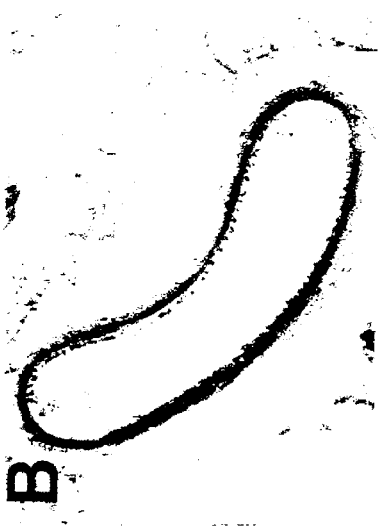
Figure 5C:
Figure 5D:
Figure 5E:
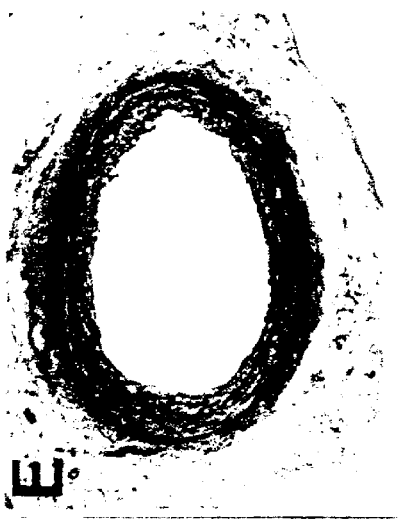
Figure 5F:
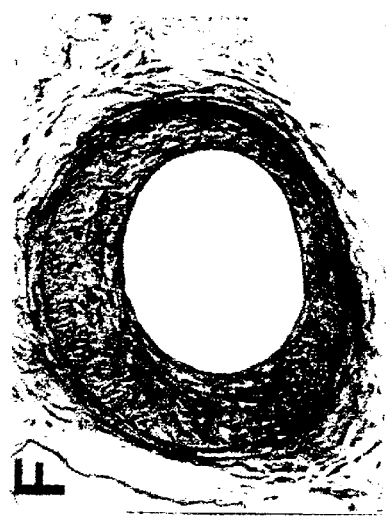
Figure 6B:
FIG. 6 is a series of cross-sectional views of the femoral artery in mice maintained on a western diet containing sulindac, 4 weeks after mechanical injury.
Figure 6D:
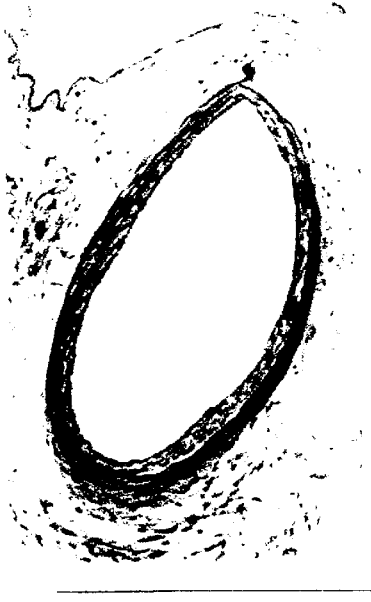
Figure 6A:
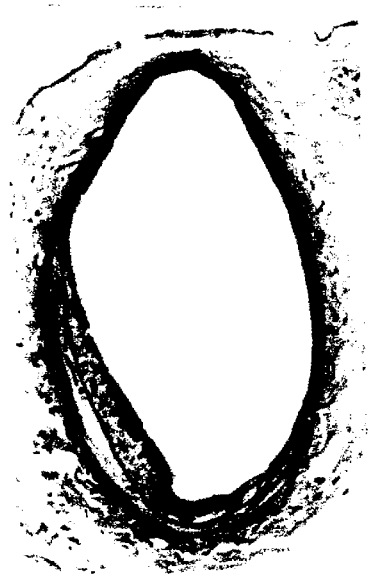
Figure 6C:
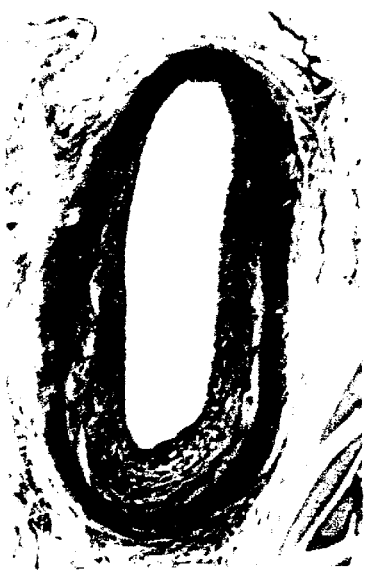

The atherosclerotic index measured as vessel wall thickness, was significantly smaller in the sulindac treated mice indicating a preventive and/or therapeutic effect of this NSAID on atherogenesis. Aspirin had a small inhibitory effect but this was not found to be significant. FIGS. 2 and 3 and Table 2.

TABLE 2

| | Wall Thickness |
|---|---|
| Control | 1.13 ± 0.19 |
| ASA | 1.01 ± 0.05 |
| Sulindac | 0.63 ± 0.01 |

These results indicate a beneficial effect of sulindac in selectively inducing apoptosis or inhibiting the proliferation, or inducing quiescence, migration or differentiation of cells in the vessel wall.

7. Effects of Sulindac and Aspirin on Restenosis in Apo-E Deficient Mice

ApoE knockout mice maintained on the Western Diet with or without additional sulindac (300 mg/kg) for 17 weeks were subjected to acute mechanical arterial injury. Four weeks later, they were sacrificed and the injured area was examined. FIG. 5 shows cross-sectional views of (A) the control non-injured femoral artery, (B) one hour after injuring the femoral artery, (C) 24 hours after injuring the femoral artery, (D) one week after injuring the femoral artery, (E) two weeks after injuring the femoral artery and (F) four weeks after injuring the femoral artery. Results obtained indicate increasing smooth muscle cell proliferation and arterial narrowing after mechanical injury, with time. However, in the mice receiving sulindac in the diet, there was much less proliferation of smooth muscle cells recorded and the narrowing of the artery was not as marked as compared with corresponding specimens from the control group. (FIGS. 6A to D). These results demonstrate that sulindac treated animals exhibit a paucity of smooth muscle cell proliferation and arterial narrowing after mechanical injury. This demonstrates a strong inhibitory effect of the drug on vascular cell proliferation.

The present invention is not to be limited in scope by the embodiments disclosed in the example which are intended as an illustration of one aspect of the invention and any methods which are functionally equivalent and within the scope of the invention. Indeed, various modifications of the invention in addition to those shown and described herein will become apparent to those skilled in the art from the foregoing description. Such modifications are intended to fall within the scope of the appended claims.

Various publications are cited herein, the disclosures of which are incorporated by reference in their entireties.

It will thus be seen that the objects set forth above, among those made apparent from the preceding description, are efficiently attained and, since certain changes may be made in carrying out the above method and in the compositions set forth without departing from the spirit and scope of the invention, it is intended that all matter contained in the above description and shown in the accompanying drawings shall be interpreted as illustrative and not in a limiting sense. It is also to be understood that the following claims are intended to cover all of the generic and specific features of the invention herein described and all statements of the scope of the invention which, as a matter of language, might be said to fall there between.

What is claimed is:

1. A method of preventing development of hyperlipidemia in an individual, the method comprising administering to the individual an effective amount of sulindac to induce hypolipidemia.

2. A method of preventing development of atherosclerosis in an individual having a region of proliferating cells, the method comprising administering to the individual an effective amount of a non-steroidal anti-inflammatory drug to induce apoptosis of the proliferating cells.

3. The method according to claim 2, wherein the non-steroidal anti-inflammatory drug is sulindac.

4. The method according to claim 2, further comprising administration of an antioxidant.

* * * * *